(12) United States Patent
Greef et al.

(10) Patent No.: US 9,754,319 B2
(45) Date of Patent: Sep. 5, 2017

(54) SOURCE DOCUMENT FRAMEWORK FOR ACCOUNTING SYSTEMS

(71) Applicant: MICROSOFT TECHNOLOGY LICENSING, LLC, Redmond, WA (US)

(72) Inventors: Arthur Greef, Seattle, WA (US); John Healy, Fargo, ND (US); David Reinhold, Sammamish, WA (US); Michael Gall, Copenhagen (DK); Manoj Swaminathan, Issaquah, WA (US); Ronald Schulz, West Fargo, ND (US)

(73) Assignee: MICROSOFT TECHNOLOGY LICENSING, LLC, Redmond, WA (US)

( * ) Notice: Subject to any disclaimer, the term of this patent is extended or adjusted under 35 U.S.C. 154(b) by 246 days.

(21) Appl. No.: 13/666,817

(22) Filed: Nov. 1, 2012

(65) Prior Publication Data

US 2013/0185178 A1    Jul. 18, 2013

Related U.S. Application Data

(60) Provisional application No. 61/588,023, filed on Jan. 18, 2012.

(51) Int. Cl.
*G06Q 40/00* (2012.01)
*G06F 19/00* (2011.01)
(Continued)

(52) U.S. Cl.
CPC ......... *G06Q 40/00* (2013.01); *G06F 17/2247* (2013.01); *G06F 17/30896* (2013.01); *G06F 19/322* (2013.01); *G06F 19/3431* (2013.01)

(58) Field of Classification Search
CPC ........ G06Q 40/12; G06Q 40/02; G06Q 40/10; G06Q 10/10; G06Q 10/067
(Continued)

(56) References Cited

U.S. PATENT DOCUMENTS

2002/0049749 A1* 4/2002 Helgeson ................ G06F 9/468
709/203
2002/0120612 A1 8/2002 Ichihara
(Continued)

OTHER PUBLICATIONS

Kusarige, Vinuthan. Client/server technology. Southern Connecticut State University, ProQuest Dissertations Publishing, 2006. 1435438.*
(Continued)

*Primary Examiner* — F. Zeender
*Assistant Examiner* — Fawaad Haider

(57) ABSTRACT

A source document framework for accounting systems is described. An apparatus may comprise an accounting application arranged for execution by the processor circuit, the ERP application comprising a source document framework component arranged to create a new source document type to add to heterogeneous source document types, and a source document process component arranged to process source documents of the heterogeneous source document types, with at least one of the heterogeneous source document types including a previous source document type arranged for use with process logic specific to the previous source document type, and process one or more source documents of the new source document type with the process logic specific to the previous source document type. Other embodiments are described and claimed.

20 Claims, 10 Drawing Sheets

(51) Int. Cl.
  *G06F 17/22* (2006.01)
  *G06F 17/30* (2006.01)
(58) Field of Classification Search
  USPC .......................................................... 705/30
  See application file for complete search history.

(56) References Cited

U.S. PATENT DOCUMENTS

| | | | |
|---|---|---|---|
| 2004/0186817 | A1 | 9/2004 | Thames |
| 2005/0060648 | A1 | 3/2005 | Fennelly |
| 2010/0161460 | A1 | 6/2010 | Vroom |
| 2010/0332360 | A1* | 12/2010 | Nowotny ........................ 705/30 |

OTHER PUBLICATIONS

P. Yuqing, W. Jiuli, Design and implementation of Accounting e-Business platform for source documents, 2010 International Conference on Computer Application and System Modeling (ICCASM), Oct. 2010, pp. V10-5-V10-8, http://ieeexplore.ieee.org/stamp/stamp.jsp?tp=&arnumber=5622916.

C. Chaudhuri & A. Chaudhuri, Detection of Verbatim or Partial Duplication from Multiple Source Documents Using Data Mining Techniques and Case-Based Reasoning Methodologies, 2011 Second International Conference on Emerging Applications of Information Technology (EAIT), Feb. 2011, pp. 129-132, http://ieeexplore.ieee.org/stamp/stamp.jsp?tp=&arnumber=5734933.

S. Russell, Paradigms for verification of authorization at source of electronic documents in an integrated environment, Eighth Annual Computer Security Applications Conference, 1992, (1992), oo, 203-209, http://ieeexplore.ieee.org/stamp/stamp.jsp?tp=&arnumber=228219.

General Accounting and Auditing System, 2012, http://www.geosolutions.com.ph/products/commercial/Commercial_gaas.html.

* cited by examiner

400

PROVIDE A SOURCE DOCUMENT FRAMEWORK FOR HETEROGENEOUS SOURCE DOCUMENT TYPES EACH CONFIGURED FOR USE WITH DEFINED PROCESSING LOGIC OF AN ENTERPRISE RESOURCE PLANNING (ERP) SYSTEM
402

DEFINE A NEW SOURCE DOCUMENT TYPE FOR THE ERP SYSTEM UTILIZING THE SOURCE DOCUMENT FRAMEWORK
404

PROCESS SOURCE DOCUMENTS OF THE NEW SOURCE DOCUMENT TYPE UTILIZING THE DEFINED PROCESSING LOGIC OF THE ERP SYSTEM
406

REFERENCE A SOURCE DOCUMENT OF THE NEW SOURCE DOCUMENT TYPE UTILIZING SOURCE DOCUMENT HEADER INFORMATION AND SOURCE DOCUMENT LINE INFORMATION OF THE SOURCE DOCUMENT FRAMEWORK
408

```
DOCUMENT CONSEQUENCES OF BUSINESS EVENT WITH
SOURCE DOCUMENT IMPLEMENTATION
502
```

```
PERSIST SOURCE DOCUMENT IMPLEMENTATION
504
```

```
PERSIST SOURCE DOCUMENT ABSTRACTION
506
```

```
REFERENCE SOURCE DOCUMENT ABSTRACTION FROM
SOURCE DOCUMENT IMPLEMENTATION
508
```

READ SOURCE DOCUMENT PROJECTION DATA SPECIFIED BY INTERFACES
602

DETERMINE JOURNAL ACCOUNTS USING SOURCE DOCUMENT PROJECTION DATA
604

PERSIST JOURNAL ACCOUNT ENTRIES
606

REFERENCE SOURCE DOCUMENT ABSTRACTION FROM JOURNAL ACCOUNT ENTRIES
608

SELECT JOURNAL ENTRIES
702

DRILL BACK TO REFERENCED SOURCE DOCUMENT ABSTRACTIONS
704

RETRIEVE SOURCE DOCUMENT IMPLEMENTATIONS
706

*FIG. 7*

SOURCE DOCUMENT FRAMEWORK FOR ACCOUNTING SYSTEMS

RELATED APPLICATION

This application claims the benefit of, and priority to, previously filed U.S. Provisional Patent Application Ser. No. 61/588,023 entitled "Source Document Framework For Accounting Systems" filed on Jan. 18, 2012, the subject matter of which is hereby incorporated by reference in its entirety.

BACKGROUND

An accounting system typically manages one or more source documents. A source document is an original record that evidences an occurrence of one or more business events in an accounting system. Source documents are entered into an accounting system that records, classifies, tracks, and reports on the economic resources exchanged or committed at a time of a business event (e.g., entry of a purchase order). There are multiple operations and administration activities that process these source documents to generate downstream register and journal entries as well as additional downstream source documents. Register and journal entries as well as downstream source documents need to reference the source documents from which they were originated.

An accounting system needs to control processing of different types of source documents. However, some types of source documents and associated processing requirements are unknown when an accounting system is developed. As new types of source documents are defined for new source document implementations, various business processes and entity types need to reference and process these new source document types. This can be difficult when the source document type was not defined at the time the business process or entity was developed. One potential solution is to create custom source documents and to create custom business processes for processing these source documents. This solution typically needs significant software development time, and usually needs the use of overlapping database foreign keys that can lead to referential integrity problems in relational database applications, both of which are undesirable features for many use scenarios. It is with respect to these and other considerations that improvements are needed to improve management of source documents and source document processing for accounting systems.

SUMMARY

The following presents a simplified summary in order to provide a basic understanding of some novel embodiments described herein. This summary is not an extensive overview, and it is not intended to identify key/critical elements or to delineate the scope thereof. Its sole purpose is to present some concepts in a simplified form as a prelude to the more detailed description that is presented later.

Various embodiments are generally directed to techniques to manage source documents and associated processing in an information system, such as a line of business (LOB) system. Some embodiments are particularly directed to techniques for implementing a source document framework for commercial accounting systems. The source document framework may be used to generically reference a source document to maintain referential integrity in a database. The source document framework can also be used to generically reference a source document to request different types of data, including without limitation business event, party, location, activity, and product term, condition and other data provided by a source document implementation without knowing the implementation details of the source document.

To the accomplishment of the foregoing and related ends, certain illustrative aspects are described herein in connection with the following description and the annexed drawings. These aspects are indicative of the various ways in which the principles disclosed herein can be practiced and all aspects and equivalents thereof are intended to be within the scope of the claimed subject matter. Other advantages and novel features will become apparent from the following detailed description when considered in conjunction with the drawings.

BRIEF DESCRIPTION OF THE DRAWINGS

FIG. 4 illustrates an embodiment of a logic flow for creating a new source document type.

FIG. 5 illustrates an embodiment of a logic flow for processing and referencing a source document from a source document implementation.

FIG. 6 illustrates an embodiment of a logic flow for processing and referencing a source document from a journal account entry.

FIG. 7 illustrates an embodiment of a logic flow for drilling back from journal entries to source document implementations.

DETAILED DESCRIPTION

Figure 1:
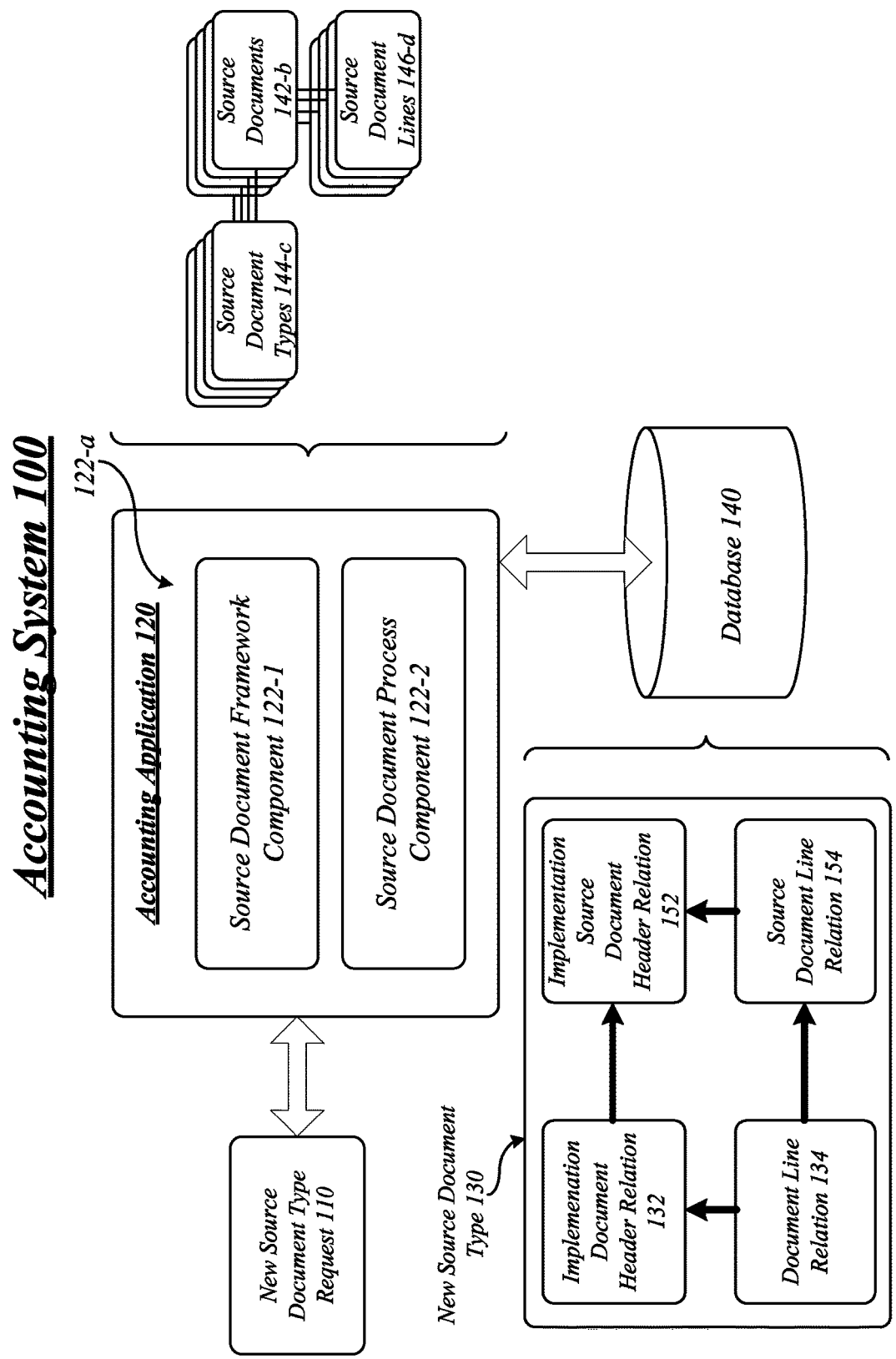
FIG. 1 illustrates an embodiment of an enterprise resource planning system.

Embodiments provide a source document framework that allows heterogeneous source document types to be referenced in a uniform way to preserve referential integrity for a database and allow business processes to access different types of data, such as business event, product, party, location, activity, and other types of data without knowledge of the implementation of a source document. The source document framework provides a capability to reference source documents in a generic and uniform way in a database using non-overlapping foreign key constraints. The source document framework also provides a capability to reference source document lines in a generic and uniform way in a database using non-overlapping foreign key constraints. The source document framework further provides a capability to identify a specific type of source document associated with a given source document reference. The source document framework still further provides a capability to identify a specific type of source document line associated with a given source document line reference. The source document framework further provides a relation type that names a source document implementation data type. The source document framework further provides a relation type that names a source document line implementation data type. Finally, the source document framework further provides a capability for source document framework processors to access business event, product, location, party, activity term, condition and other data on source document implementations without prior knowledge of a specific structure used for different source document implementations. Other embodiments are described and claimed.

With general reference to notations and nomenclature used herein, the detailed descriptions which follow may be presented in terms of program procedures executed on a computer or network of computers. These procedural descriptions and representations are used by those skilled in the art to most effectively convey the substance of their work to others skilled in the art.

A procedure is here, and generally, conceived to be a self-consistent sequence of operations leading to a desired result. These operations are those requiring physical manipulations of physical quantities. Usually, though not necessarily, these quantities take the form of electrical, magnetic or optical signals capable of being stored, transferred, combined, compared, and otherwise manipulated. It proves convenient at times, principally for reasons of common usage, to refer to these signals as bits, values, elements, symbols, characters, terms, numbers, or the like. It should be noted, however, that all of these and similar terms are to be associated with the appropriate physical quantities and are merely convenient labels applied to those quantities.

Further, the manipulations performed are often referred to in terms, such as adding or comparing, which are commonly associated with mental operations performed by a human operator. No such capability of a human operator is necessary, or desirable in most cases, in any of the operations described herein which form part of one or more embodiments. Rather, the operations are machine operations. Useful machines for performing operations of various embodiments include general purpose digital computers or similar devices.

Various embodiments also relate to apparatus or systems for performing these operations. This apparatus may be specially constructed for the required purpose or it may comprise a general purpose computer as selectively activated or reconfigured by a computer program stored in the computer. The procedures presented herein are not inherently related to a particular computer or other apparatus. Various general purpose machines may be used with programs written in accordance with the teachings herein, or it may prove convenient to construct more specialized apparatus to perform the required method steps. The required structure for a variety of these machines will appear from the description given.

Reference is now made to the drawings, wherein like reference numerals are used to refer to like elements throughout. In the following description, for purposes of explanation, numerous specific details are set forth in order to provide a thorough understanding thereof. It may be evident, however, that the novel embodiments can be practiced without these specific details. In other instances, well known structures and devices are shown in block diagram form in order to facilitate a description thereof. The intention is to cover all modifications, equivalents, and alternatives consistent with the claimed subject matter.

FIG. 1 illustrates a block diagram for an accounting system 100. In one embodiment, the accounting system 100 may comprise a computer-implemented accounting system having an accounting application 120 comprising one or more components 122-a. The accounting application 120 may be implemented, for example, in an accounting application server, among other electronic devices. An example of an accounting system may include, among others, an enterprise resource planning (ERP) ERP system. Although the accounting system 100 shown in FIG. 1 has a limited number of elements in a certain topology, it may be appreciated that the accounting system 100 may include more or less elements in alternate topologies as desired for a given implementation.

It is worthy to note that "a" and "b" and "c" and similar designators as used herein are intended to be variables representing any positive integer. Thus, for example, if an implementation sets a value for a=5, then a complete set of components 122-a may include components 122-1, 122-2, 122-3, 122-4 and 122-5. The embodiments are not limited in this context.

The accounting system 100 may be generally arranged to integrate internal and external management information across an entity, such as a business organization, for example. With respect to a business organization, the accounting system 100 may manage various types of organization information, such as business information, finance information, accounting information, manufacturing information, sales and service information, customer relationship management (CRM) information, and so forth. Specific examples of organization information may include without limitation a business event, product, party, location, activity, and other types of data relevant to an organization. The accounting system 100 automates this activity with an integrated software application, referred to herein as an accounting application 120. One goal of the accounting system 100 is to facilitate the flow of information between all entity functions inside the boundaries of the entity and manage the connections to outside entities (e.g., vendors, suppliers, customers, etc.).

In various configurations, the accounting system 100 can be implemented on a variety of computer hardware, software and network platforms, typically employing one or more accounting servers (e.g., application object servers, file servers, database servers, mid-tier servers, etc.) to implement process logic (e.g., business logic) and one or more databases (e.g., a relational database management system) as a repository for business information managed by the accounting system 100. Various types of client devices, as described below with reference to FIG. 8, may be used to interact with the various ERP servers to create, access, modify or otherwise manage the organization information utilizing a variety of functions, methods and/or services provided by the accounting system 100.

The accounting system 100 may include an accounting application 120. In various embodiments, the accounting application 120 may comprise a software application arranged for execution by a logic device (e.g., a processor circuit) to provide various types of applications and/or services for the accounting system 100. Examples of applications and/or services may include without limitation finance and accounting, human resources, manufacturing, supply chain management, project management, customer relationship management, data services, access control, business intelligence, and security, among others. One example of a suitable accounting application 120 may comprise an ERP application, such as MICROSOFT® DYNAMICS® AX, made by MICROSOFT CORPORATION, Redmond, Wash., among others. In one embodiment, for example, the accounting application 120 may comprise a commercial accounting application and/or service, offering such functions as general ledger, payables, cash management, fixed assets, receivables, budgeting, consolidation, and other standard accounting features. The embodiments are not limited to the examples given above.

The accounting application 120 may be generally arranged to manage source documents 142-b and source document lines 146-d stored by a local or remote database 140. In one embodiment, the database 140 may be implemented as a database management system (DBMS), such as a relational database management system (RDBMS), for example. Other DBMS techniques may be used as well.

A source document 142-b is an original record that evidences an occurrence of one or more business events in the accounting system 100, such as a commercial accounting system, for example. Source document lines 146-d are associated with a source document 142-b, such as a specific portion of a source document 142-b, for example. Source documents 142-b and associated source document lines 146-d are entered into an accounting system that records, classifies, tracks, and reports on the economic resources exchanged or committed at a time of a business event (e.g., entry of a purchase order). There are multiple operations and administration activities that process the source documents 142-b to generate downstream register and journal entries as well as additional downstream source documents 142-b. In many if not all cases, register and journal entries as well as downstream source documents 142-b need to reference the source documents 142-b from which they were originated.

The source documents 142-b and source document lines 146-d may comprise various heterogeneous source document types 144-c. Examples of source document types 144-c may include without limitation purchase orders, purchase agreements, vendor requests, accounting events, accounting distributions, vendor invoices, customer invoices, and so forth. Any number of different source document types 144-c may be developed for a given implementation of the accounting application 120, and the embodiments are not limited in this context.

The accounting application 120 may comprise a source document framework component 122-1. The source document framework component 122-1 may be generally arranged to provide a source document framework capable of creating new source document types 144-c to seamlessly add to the heterogeneous source document types 144-c already created for the accounting application 120, as well as any associated logic, processes, methods or services.

As previously described, an accounting system needs to control processing of different source document types 144-c of source documents 142-b and/or source document lines 154. However, a case may arise where certain source documents types 144-c and associated processing requirements are unknown when an accounting system is developed. As new source document types 144-c are defined for new source document implementations, various business processes and entity types need to reference and process these new source document types 144-c. For example, a journal entry may need to reference a purchase order. This can be difficult when a given source document type 144-c was not defined at the time the business process or entity was developed.

The source document framework component 122-1 provides a set of extension points that allow new source document types 144-c that may be used with business processes, supporting business logic, entity types and other properties and/or characteristics of the accounting application 120 that have been defined previous to creation of the new source document type 144-c. In one embodiment, for instance, the new source document type 144-c may utilize business logic (e.g., methods, functions, modules, etc.) arranged for use with business logic specific to a previously existing source document type 144-c. In this manner, the source document framework component 122-1 may reduce or eliminate any need for custom source documents and custom business processes for processing these source documents, and associated software development time. Further, the source document framework component 122-1 may reduce or eliminate any need to use overlapping database foreign keys that can lead to referential integrity problems in relational database applications.

The source document framework component 122-1 may implement an improved source document framework that provides new source document type 130 that provides referential integrity for the database 140 and allow business processes to access different types of data, such as business event, product, party, location, activity, and other types of data without knowledge of the implementation of a source document 142-b. The source document framework provides a capability to reference source documents 142-b in a generic and uniform way in the database 140 using non-overlapping foreign key constraints. The source document framework also provides a capability to reference source document lines 146-d in a generic and uniform way in a database using non-overlapping foreign key constraints. The source document framework further provides a capability to identify a specific type of source document 142-b associated with a given source document reference. The source document framework still further provides a capability to identify a specific type of source document line relation 146-d associated with a given source document line reference. The source document framework further provides a relation type that names a source document implementation data type. The source document framework further provides a relation type that names a source document line implementation data type. Finally, the source document framework further provides a capability for source document framework processors to access business event, product, location, party, activity term, condition and other data on source document implementations without prior knowledge of a specific structure used for different source document implementations.

To provide these and other advantages, the source document framework component 122-1 may implement at least two abstract relation types. More particularly, the source document framework component 122-1 may utilize a pair of new relation types (e.g., tables) referred to as a source document header relation 152 and a source document line relation 154. The source document header relation 152 may be used to maintain referential integrity for source documents 142-b of heterogeneous source document types 144-c. The source document line relation 154 may be used to maintain referential integrity for a source document line 146-d associated with a source document 142-b of heterogeneous source document types 144-c. Examples and uses for the source document header relation 152 and the source document line relation 154 may be described in more detail with reference to FIGS. 2A, 2B.

The accounting application 120 may include a source document process component 122-2 arranged to process source documents 142-b of the heterogeneous source document types 144-c. When a source document type 144-c is created for the accounting application 120, there may be a set of business resources defined for the source document type 144-c, such as custom business processes, business logic, tables, headers, entity types, and other resources that are implemented to support the source document type 144-c. For instance, if a source document type 144-1 is a purchase order, there may be various software objects, tables, and associated methods used to process "downstream" events for a purchase order, such as creating a purchase order, tracking a purchase order, tracking delivery dates for goods or services defined in a purchase order, accounting events for the purchase order, and so forth. Similarly, if a source document type 144-2 is a customer order, there may be common, similar or different software objects, tables and associated methods used to process downstream events for a customer order. The source document process component 122-2 is arranged to process source documents 142-b of heterogeneous source document types 144-c in accordance with associated business resources defined for the source document types 144-c.

In one embodiment, at least one of the heterogeneous source document types 144-c may include a previous source document type 144-c arranged for use with business logic specific to the previous source document type 144-c. In this case, the source document process component 122-2 may process one or more source documents 142-b of a new source document type 144-c with business logic specific to the previous source document type 144-c. For instance, assume a source document type 144-1 is arranged for use with business logic specific to the source document type 144-1. When a new source document type 144-2 is created, the source document process component 122-2 may process one or more source documents 142-b of the new source document type 144-2 with business resources typically performed for the previous source document type 144-1.

For example, the source document framework may provide common processing control that each source document implementation does not need to implement as in traditional accounting systems. The source document framework may provide processing control logic, while the implementation just needs to provide data when the control logic asks for it. Implementations do not need to implement processing control logic.

In general operation, the accounting application 120 may receive a new source document type request 110, and automatically create a new source document type 130 in response to the new source document type request 110. Alternatively, a developer may manually create a new source document type 130 via framework extension points.

In one embodiment, the source document framework component 122-1 may receive the new source document request 110, process the new source document request 110, and create a new source document type 130. The new source document type 130 may include four relation types, including an implementation document header relation 132, an implementation document line relation 134, a source document header relation 152 and a source document line relation 154. The implementation document header relation 132 and the implementation document line relation 134 may be used to persist data for a source document 142-b and source document line 146-d, respectively. Examples and uses for the document header information 132 and document line information 134 may be further described with reference to FIGS. 2A, 2B.

Figure 2A:
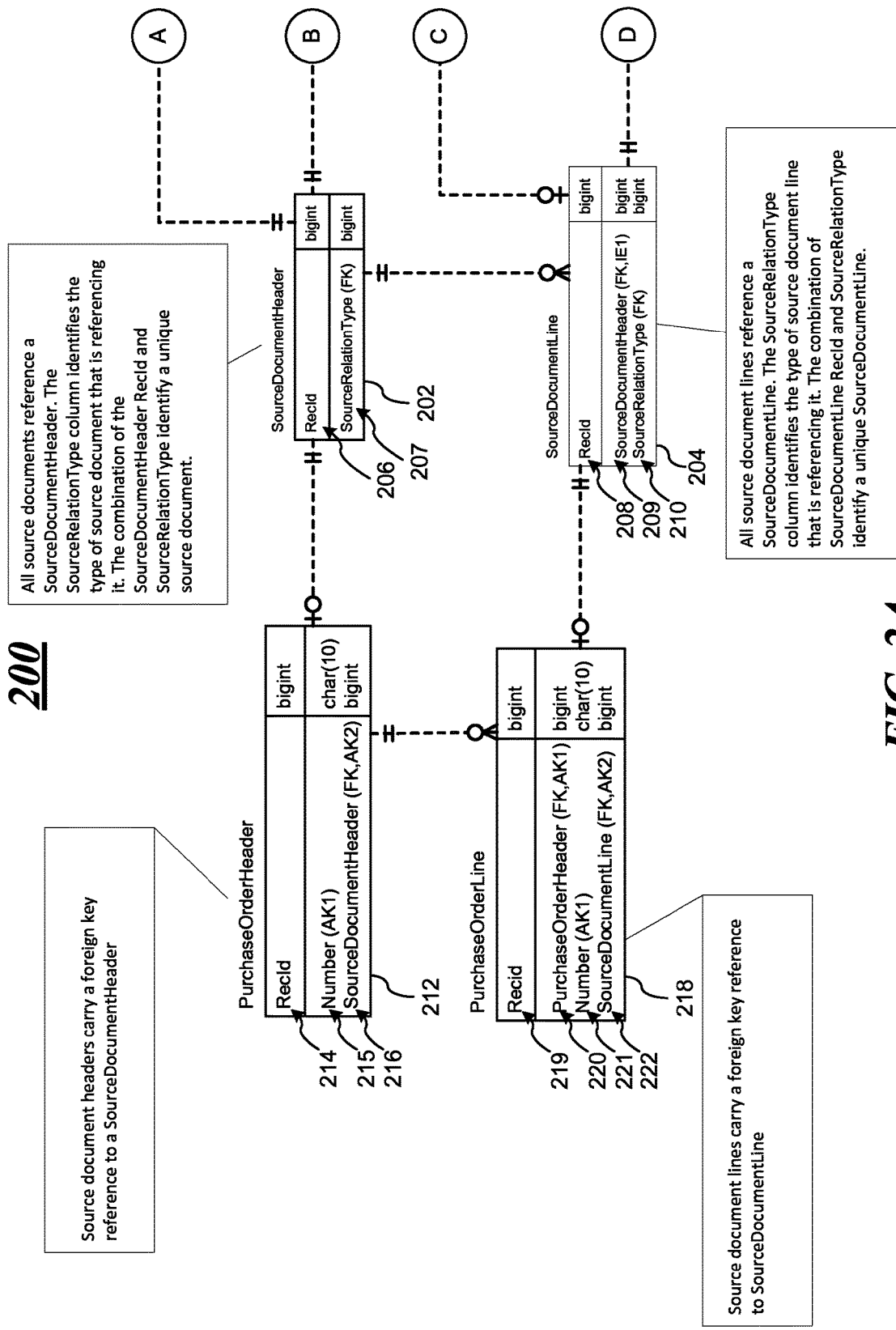
FIG. 2A illustrates an embodiment of a source document data model.
Figure 2B:
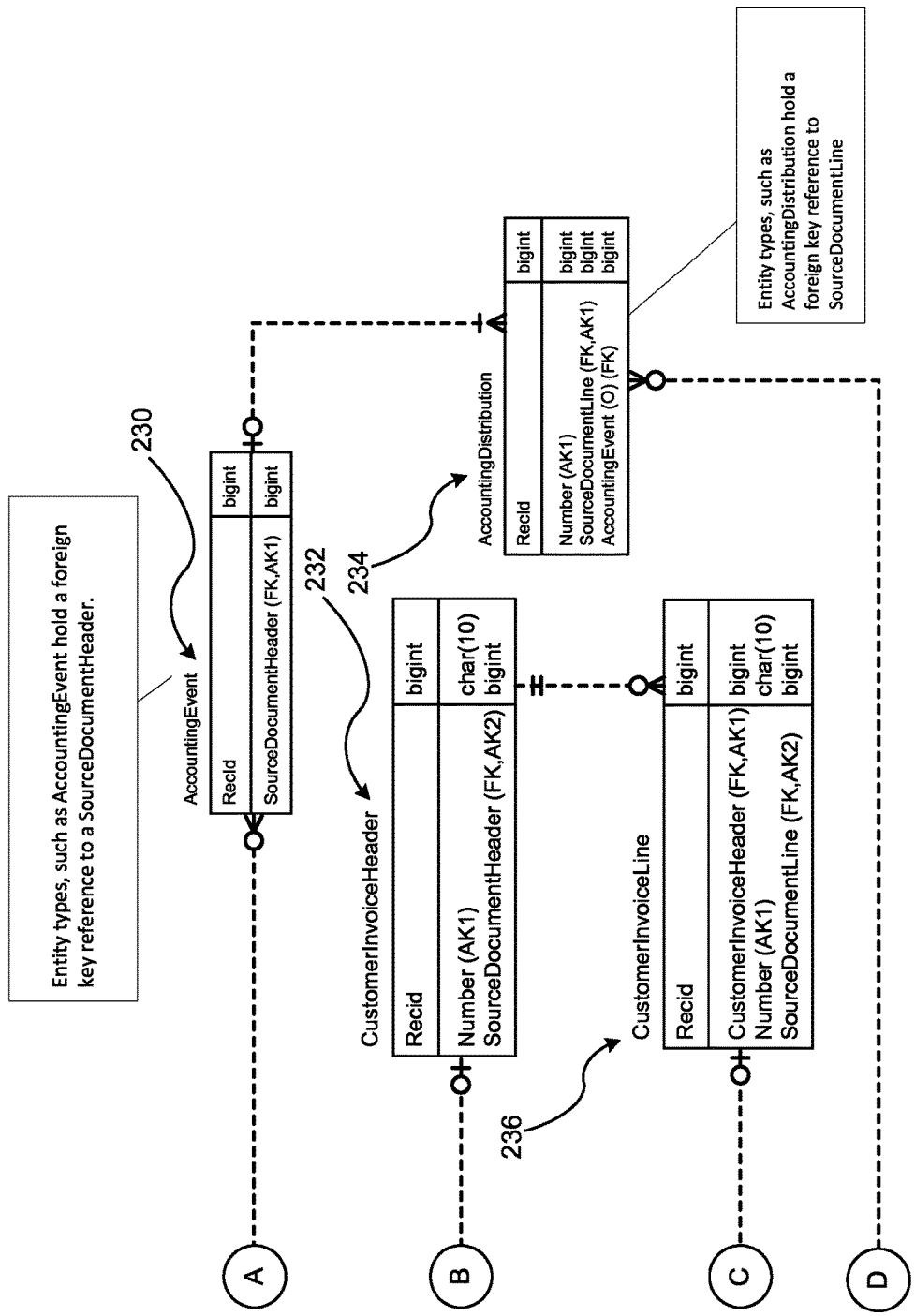
FIG. 2B illustrates an embodiment of a source document data model.

FIGS. 2A, 2B illustrate a source document data model 200. As shown in FIGS. 2A, 2B, a source document framework may provide at least two abstract relation types. The first abstract relation type is a source document header relation 202, which is an example for the source document header relation 152 referred to in FIG. 1. The second abstract relation type is a source document line relation 204, which is an example for the source document line relation 154 referred to in FIG. 1. Both of these abstract relation types can be referenced by other relation types, such as a document header relation 212 and/or a document line relation 218, which are examples for the implementation document header relation 132 and the implementation document line relation 134, respectively, referred to in FIG. 1.

As shown in FIG. 2A, the source document framework component 122-1 may provide an exemplary source document header relation 202 with source document header information for storing data associated with multiple heterogeneous source documents 142-b and source document types 144-c. The source document header relation 202 may comprise a new relation type (e.g., table) for the database 140. The source document header information may include, among other information, a source document header record identifier field 206 and a source relation type field 207. The source relation type field 207 may comprise a foreign key. Further, the source document framework component 122-1 may provide an exemplary source document line relation 204 with source document line information for storing data associated with heterogeneous source document lines 146-d. The source document line relation 204 may comprise another new relation type (e.g., table) for the database 140. The source document line information may include, among other information, a source document line record identifier field 208, a source document header field 209, and a source relation type field 210. The source document header field 209 and the source relation type field 210 may both be implemented as foreign keys.

The source document header relation 202 and the source document line relation 204 may be used to create new source document types 144-c for source documents 142-b and/or source document lines 146-d for use by the accounting application 120 of the accounting system 100. For instance, the source document framework component 122-1 may receive a new source document type request 110. The new source document type request 110 may comprise a request to create a new source document type 144-c, a source document 142-b of a new source document type 144-c, or a source document line relation 146-d of a new source document type 144-c. The source document framework component 122-1 may pass the new source document type request 110 to the source document framework component 122-1. The source document framework component 122-1 may create and store a document header relation 212 with document header information for a source document 142-1 of the new source document type 144-1. The document header information may include, among other information, a source document header field 214 of type source document header record identifier 206, a number field 215, and a source document header field 216 of type source document header relation 202. The source document framework component 122-1 may also create and store a document line relation 218 with document line information for a source document line 146-1 associated with the source document 142-1 of the new source document type 144-1. The document line information may include, among other information, a source document line field 219 of type source document line record identifier 208, a document header field 220 of type document header relation 212, a number field 221, and a source document line field 222 of type source document line relation 204.

Once the document header relation 212 and the document line relation 218 are created for the source document 142-1 and the source document line 146-1, respectively, these relations may be used to reference the source document 142-1 of the new source document type 144-1 utilizing the source document header information and the source document line information of the source document framework stored by the source document header relation 202 and the source document line relation 204, respectively.

More particularly, one or more source document implementation relation types may utilize a non-overlapping foreign key reference to a source document header relation 202. Similarly, one or more source document line implementation relation types may utilize a non-overlapping foreign key reference to a source document line relation 204. The source document header relation 202 and the source document line relation 204 relation types each have a source relation type column that identifies a relation type of the source document or source document line to which it is related, examples of which are provided by Tables 1-8 below. The relation types may be enumerated in accordance with any given enumeration technique (e.g., 101, 102, 103, etc.).

Entity types generated from source documents 142-b or source document lines 146-d processing hold a non-overlapping foreign key reference to a source document header relation 202 and/or a source document line relation 204 relation types. The specific source document implementation type to which a source document header relation 202 or source document line relation 204 tuple is related is specified by the source relation type column on the source document header relation 202 and source document line relation 204 tables. The source relation type identifies the type or category of source document implementation but not a specific document. The combination of the source relation type and the source document header record identifier 206 or source document line record identifier 208, for which there is a foreign key reference from the implementation source document header/source document line, identifies a specific source document/source document line implementation.

Selecting a relation type identified by the source relation type, and restricting the selection based on the source document header relation 202 or source document line relation 204 record identifiers (RecIDs) 206, 208, respectively, results in a return of a specific tuple associated with the source document header relation 202 or source document line relation 204. Referential integrity is maintained because a source document 142-b and a source document line relation 146-d implementation maintains a 1:1 relationship with a source document header relation 202 or source document line relation 204 relation type, respectively. This identifies a specific tuple in the source document header relation 202 or source document line relation 204 relation types to which the source document 142-b or source document line relation 146-d implementation is associated.

FIG. 2A illustrates a sample implementation of a document header relation 212 and a document line relation 218. The relations shown in FIG. 2A illustrate the source document 142-1 as a purchase order, the document header relation 212 as a purchase order header, and the document line relation 218 as a purchase order line. FIG. 2B illustrates other sample implementations of a document header relation 212 and/or a document line relation 218, including an accounting event 230, a customer invoice header 232, an accounting distribution 234, and a customer invoice line 226. It may be appreciated that these are merely a few examples, and others exist as well. The embodiments are not limited in this context.

Figure 3:
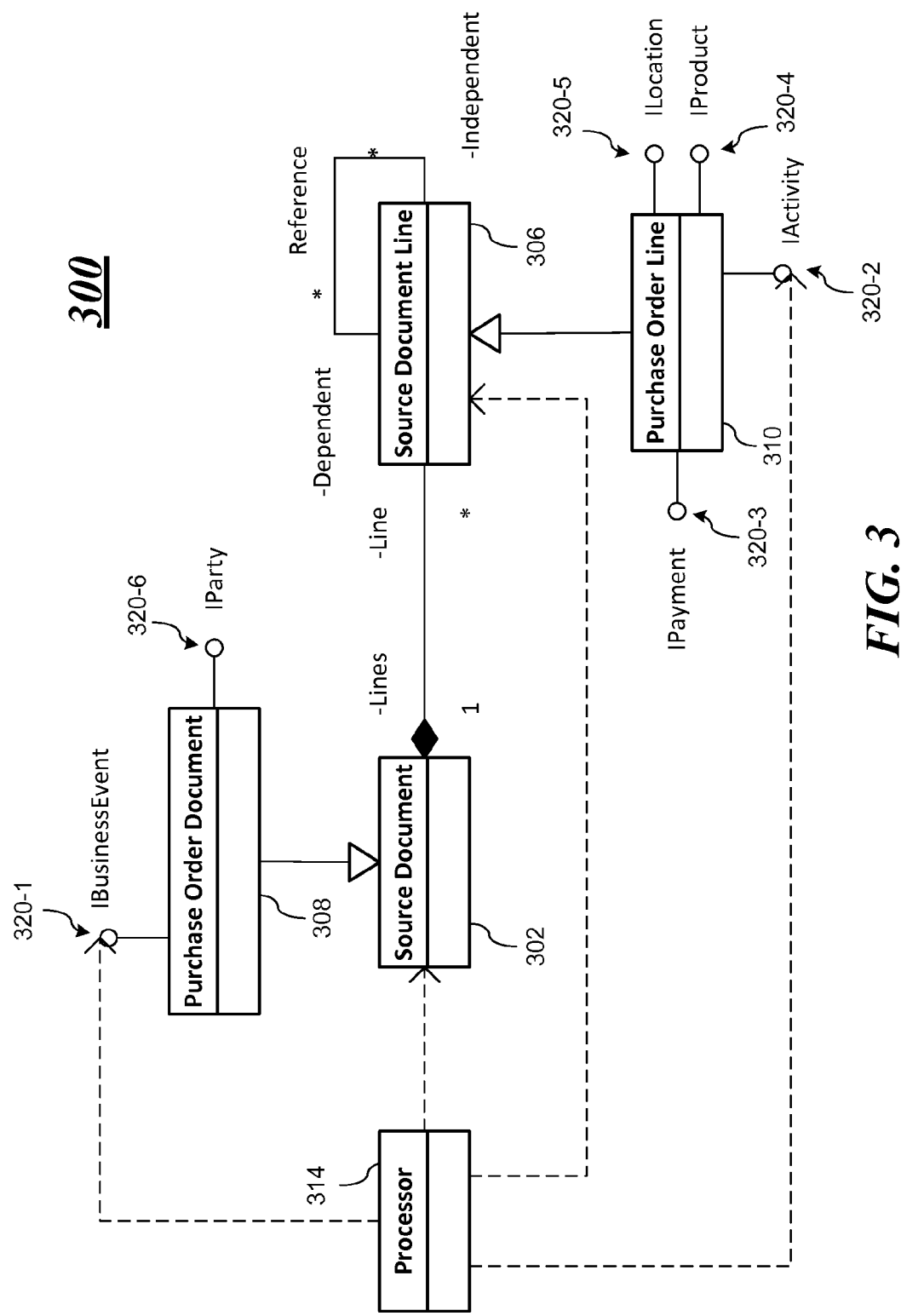
FIG. 3 illustrates an embodiment of a source document object model.

FIG. 3 illustrates a source document object model 300. Embodiments also provide different object types, including a source document object 302 and a source document line object 306. The source document framework component 122-1 provides various interfaces 320-e for accessing information provided by various source document implementations, such as a purchase order line 310. For instance, various interfaces 320-e may be provided for accessing business event, product, party, location, activity term, condition and data provided by the various source document implementations. Some examples of interfaces 320-e may include an iBusinessEvent interface 320-1 for the purchase order document 308, an iActivity interface 320-2 for the purchase order line 310, an iPayment interface 320-3 for the purchase order line 310, an iProduct interface 320-4 for the purchase order line 310, an iLocation interface 320-5 for the purchase order line 310, and an iParty interface 320-6 for the purchase order document 308. One or more operations and administrative processors 314 may reference source document implementations using the source document framework component 222-2 and access business event, product, party, location, activity term, condition and data provided by source document implementations. Although dependency arrows are shown from the operations and administrative processors 314 to two of the interfaces 320-1, 320-2, it may be appreciated that during implementation there should be connections between the operations and administrative processors 314 and all of the interfaces 320-e. The data and references in the source document objects are stored in the source document relation types described above.

An alternative implementation to the above relation types is to use a non-relational database to create, read, update and delete source document headers, lines and relationships. An alternative to using interfaces for accessing business event, product, party, location, activity term, condition and data provided by source document implementations is to use virtual methods on base source document, source document header and source document line classes.

The following tables 1-6 provide sample data for various source document implementations, including a purchase order and a customer invoice. The source document implementations may demonstrate how a source document header and a source document line rows can refer to different relation types. It may be appreciated that these are merely samples, and other source document implementations and associated data may be used for a given implementation. The embodiments are not limited in this context.

TABLE 1

PurchaseOrderHeader (RelationType = 100)

| RecId | Number | SourceDocumentHeader |
|-------|--------|----------------------|
| 10001 | 1200   | 30001                |
| 10002 | 1201   | 30002                |
| 10003 | 1202   | 30003                |

TABLE 2

PurchaseOrderLine (RelationType = 101)

| RecId | PurchaseOrderHeader | Number | SourceDocumentLine |
|-------|---------------------|--------|--------------------|
| 20001 | 10001               | 1      | 40001              |
| 20002 | 10001               | 2      | 40002              |
| 20003 | 10002               | 1      | 40003              |
| 20004 | 10003               | 1      | 40004              |
| 20005 | 10003               | 2      | 40005              |
| 20006 | 10003               | 3      | 40006              |

TABLE 3

SourceDocumentHeader

| RecId | SourceRelationType |
|---|---|
| 30001 | 100 |
| 30002 | 100 |
| 30003 | 100 |
| 30004 | 102 |

TABLE 4

SourceDocumentLine

| RecId | SourceDocumentHeader | SourceRelationType |
|---|---|---|
| 40001 | 30001 | 101 |
| 40002 | 30001 | 101 |
| 40003 | 30002 | 101 |
| 40004 | 30003 | 101 |
| 40005 | 30003 | 101 |
| 40005 | 30003 | 101 |
| 40006 | 30004 | 103 |
| 40007 | 30004 | 103 |

TABLE 5

CustomerInvoiceHeader (RelationType-102)

| RecId | Number | SourceDocumentHeader |
|---|---|---|
| 50001 | 1001 | 30004 |

TABLE 6

CustomerInvoiceLine (RelationType = 103)

| RecId | CustomerInvoiceHeader | Number | SourceDocumentLine |
|---|---|---|---|
| 60001 | 50001 | 1 | 40006 |
| 60002 | 50001 | 2 | 40007 |

The following tables 7, 8 provide sample data for various source document implementations, including a business event and accounting distribution. The source document implementations may demonstrate how a source document header and a source document line rows can refer to different relation types. It may be appreciated that these are merely samples, and other source document implementations and associated data may be used for a given implementation. The embodiments are not limited in this context.

TABLE 7

AccountingEvent

| RecId | SourceDocumentHeader |
|---|---|
| 70001 | 30001 |
| 70002 | 30002 |
| 70003 | 30003 |
| 70004 | 30004 |

TABLE 8

AccountingDistribution

| RecId | AccountingEvent | SourceDocumentLine |
|---|---|---|
| 80001 | 70001 | 4001 |
| 80002 | 70001 | 4001 |
| 80003 | 70002 | 4003 |
| 80004 | 70002 | 4003 |

Included herein is a set of flow charts representative of exemplary methodologies for performing novel aspects of the disclosed architecture. While, for purposes of simplicity of explanation, the one or more methodologies shown herein, for example, in the form of a flow chart or flow diagram, are shown and described as a series of acts, it is to be understood and appreciated that the methodologies are not limited by the order of acts, as some acts may, in accordance therewith, occur in a different order and/or concurrently with other acts from that shown and described herein. For example, those skilled in the art will understand and appreciate that a methodology could alternatively be represented as a series of interrelated states or events, such as in a state diagram. Moreover, not all acts illustrated in a methodology may be required for a novel implementation.

FIG. 4 illustrates one embodiment of a logic flow 400. The logic flow 400 may be representative of some or all of the operations executed by one or more embodiments described herein.

In the illustrated embodiment shown in FIG. 4, the logic flow 400 may provide a source document framework for heterogeneous source document types each configured for use with defined process logic of an enterprise resource planning (ERP) system at block 402. For example, the source document framework component 222-2 may provide a source document framework for heterogeneous source document types 144-c each configured for use with defined process logic of the accounting system 100. The defined process logic may comprise, for example, any number of multiple operations and administration activities that are used by the accounting application 120 to process these source documents, as well as additional downstream source documents.

The source document framework may include, for example, a source document header relation 202 with source document header information for the heterogeneous source document types 144-c, the source document header information including a source document header record identifier field 206 and a source relation type field 207. The source document framework may further include, for example, a source document line relation 204 with source document line information for the heterogeneous source document types 144-c, the source document line information including a source document line record identifier field 208, a source document header field 209 of type source document header relation 202, and a source relation type field 210.

The logic flow 400 may define a new source document type for the ERP system utilizing the source document framework at block 404. For example, the source document framework component 222-2 may receive a new source document type request 110 to define a new source document type 144-c for the accounting application 120 of the accounting system 100. The new source document type request 110 may be automatically processed by the accounting application 120, versus manual creation of new document types 144-c and custom modifications to downstream associated business logic used by the accounting application 120 needed by conventional ERP systems.

The logic flow 400 may process source documents of the new source document type utilizing the defined process logic of the ERP system at block 406. For example, the source document framework component 222-2 may process source documents 142-b (and/or source document lines 146-d) of the new source document type 144-c utilizing the defined process logic of the accounting system 100. For instance, the defined process logic may comprise logic arranged to generate downstream register and journal entries, among other types of logic.

As an example of block 406, the logic flow 400 may reference a source document interface implemented by the new source document type utilizing source document header information and source document line information of the source document framework at block 408. For example, the source document framework component 222-2 may reference a source document 142-b and/or source document line 146-d of the new source document type 144-c utilizing source document header information and source document line information provided by the source document header relation 152 (or 202) and source document line relation 154 (or 204), respectively, of the source document framework.

FIG. 5 illustrates an embodiment of a logic flow 500 for referencing a source document from a source document implementation. As shown in FIG. 5, the logic flow 500 may document consequences of a business event with a source document implementation at block 502. The consequences may include various types of logic associated with processing the business event, as managed by the source document process component 122-2, for example. The logic flow 500 may persist the source document implementation at block 504, such as in the database 140, for example. The logic flow 500 may persist a source document abstraction and accounting distributions at block 506, such as a source document header relation 152 stored in the database 140, for example. The logic flow 500 may reference the source document abstraction from the source document implementation at block 508.

FIG. 6 illustrates an embodiment of a logic flow 600 for processing and then referencing a source document from a journal account entry. As shown in FIG. 6, the logic flow 600 may read source document projection data specified by one or more interfaces at block 602, such as interfaces 320-e, for example. The logic flow 600 may determine journal accounts using the source document projection data at block 604. The logic flow 600 may persist one or more journal account entries at block 606, such as the database 140, for example. The logic flow 600 may reference accounting distributions from the journal account entries at block 608.

FIG. 7 illustrates an embodiment of a logic flow 700 for drilling back from journal entries to source document implementations. As shown in FIG. 7, the logic flow 700 selects one or more journal entries at block 702, such as the journal entries described with reference to FIG. 6. The logic flow 700 drills back to referenced source document abstractions referenced by accounting distributions at block 704. The logic flow 700 retrieves source document implementations at block 706 utilizing the source document abstractions.

Figure 8:
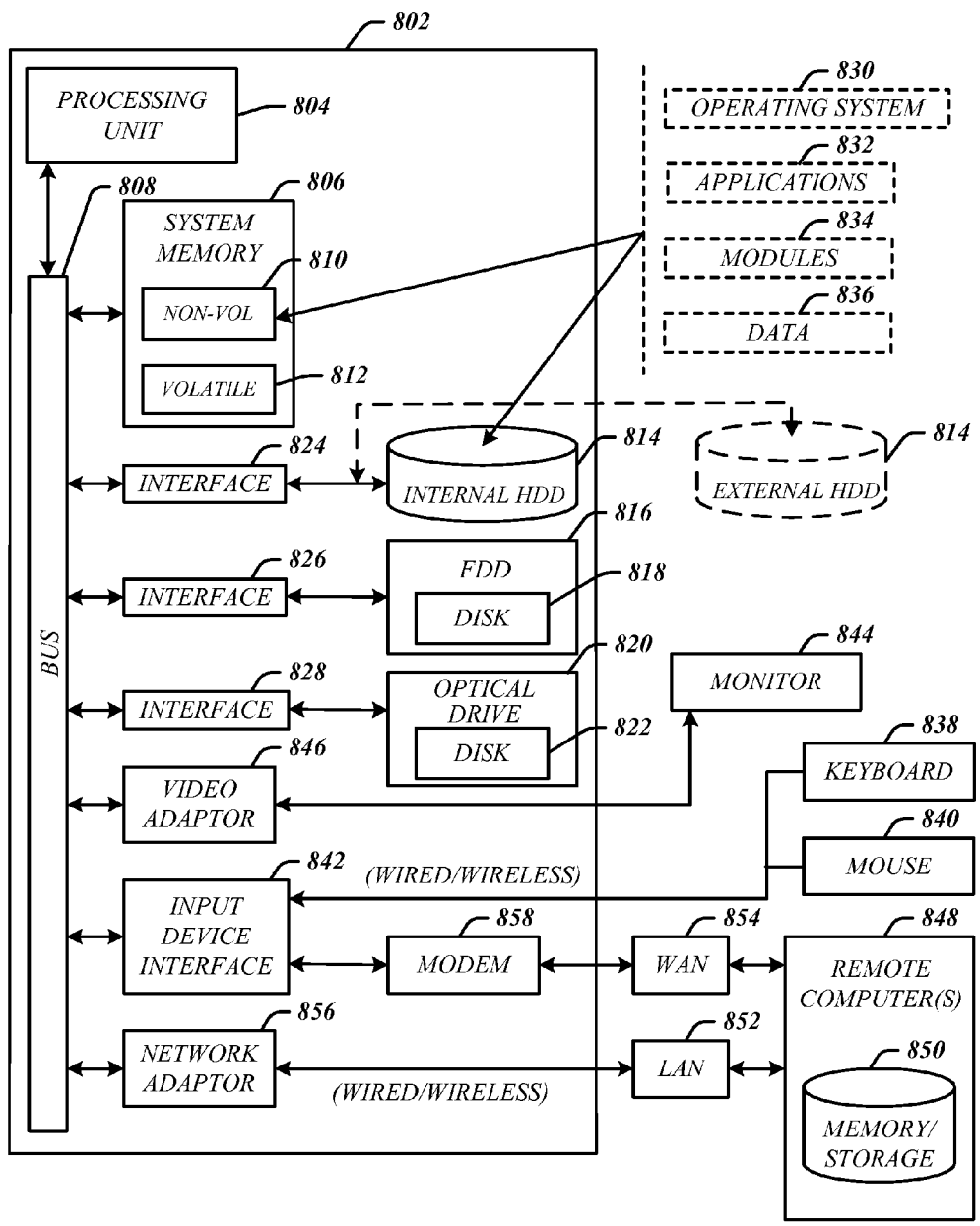
FIG. 8 illustrates an embodiment of a computing architecture.

FIG. 8 illustrates an embodiment of an exemplary computing architecture 800 suitable for implementing various embodiments as previously described. In one embodiment, the computing architecture 800 may comprise or be implemented as part of an electronic device capable of receiving, processing, and sending information for the accounting system 100. Examples of an electronic device may include without limitation an ultra-mobile device, a mobile device, a personal digital assistant (PDA), a mobile computing device, a smart phone, a telephone, a digital telephone, a cellular telephone, eBook readers, a handset, a one-way pager, a two-way pager, a messaging device, a computer, a personal computer (PC), a desktop computer, a laptop computer, a notebook computer, a netbook computer, a handheld computer, a tablet computer, a server, a server array or server farm, a web server, a network server, an Internet server, a work station, a mini-computer, a main frame computer, a supercomputer, a network appliance, a web appliance, a distributed computing system, multiprocessor systems, processor-based systems, consumer electronics, programmable consumer electronics, game devices, television, digital television, set top box, wireless access point, base station, subscriber station, mobile subscriber center, radio network controller, router, hub, gateway, bridge, switch, machine, or combination thereof. The embodiments are not limited in this context.

As used in this application, the terms "system" and "component" are intended to refer to a computer-related entity, either hardware, a combination of hardware and software, software, or software in execution, examples of which are provided by the exemplary computing architecture 800. For example, a component can be, but is not limited to being, a process running on a processor, a processor, a hard disk drive, multiple storage drives (of optical and/or magnetic storage medium), an object, an executable, a thread of execution, a program, and/or a computer. By way of illustration, both an application running on a server and the server can be a component. One or more components can reside within a process and/or thread of execution, and a component can be localized on one computer and/or distributed between two or more computers. Further, components may be communicatively coupled to each other by various types of communications media to coordinate operations. The coordination may involve the uni-directional or bi-directional exchange of information. For instance, the components may communicate information in the form of signals communicated over the communications media. The information can be implemented as signals allocated to various signal lines. In such allocations, each message is a signal. Further embodiments, however, may alternatively employ data messages. Such data messages may be sent across various connections. Exemplary connections include parallel interfaces, serial interfaces, and bus interfaces.

The computing architecture 800 includes various common computing elements, such as one or more processors, multi-core processors, co-processors, memory units, chipsets, controllers, peripherals, interfaces, oscillators, timing devices, video cards, audio cards, multimedia input/output (I/O) components, power supplies, and so forth. The embodiments, however, are not limited to implementation by the computing architecture 800.

As shown in FIG. 8, the computing architecture 800 comprises a processing unit 804, a system memory 806 and a system bus 808. The processing unit 804 can be any of various commercially available processors, including without limitation an AMD® Athlon®, Duron® and Opteron® processors; ARM® application, embedded and secure processors; IBM® and Motorola® DragonBall® and PowerPC® processors; IBM and Sony® Cell processors; Intel® Celeron®, Core (2) Duo®, Itanium®, Pentium®, Xeon®, and XScale® processors; and similar processors. Dual microprocessors, multi-core processors, and other multi-processor architectures may also be employed as the processing unit 804.

The system bus 808 provides an interface for system components including, but not limited to, the system memory 806 to the processing unit 804. The system bus 808 can be any of several types of bus structure that may further interconnect to a memory bus (with or without a memory controller), a peripheral bus, and a local bus using any of a variety of commercially available bus architectures. Interface adapters may connect to the system bus 808 via a slot architecture. Example slot architectures may include without limitation Accelerated Graphics Port (AGP), Card Bus, (Extended) Industry Standard Architecture ((E)ISA), Micro Channel Architecture (MCA), NuBus, Peripheral Component Interconnect (Extended) (PCI(X)), PCI Express, Personal Computer Memory Card International Association (PCMCIA), and the like.

The computing architecture 800 may comprise or implement various articles of manufacture. An article of manufacture may comprise a computer-readable storage medium to store logic. Examples of a computer-readable storage medium may include any tangible media capable of storing electronic data, including volatile memory or non-volatile memory, removable or non-removable memory, erasable or non-erasable memory, writeable or re-writeable memory, and so forth. Examples of logic may include executable computer program instructions implemented using any suitable type of code, such as source code, compiled code, interpreted code, executable code, static code, dynamic code, object-oriented code, visual code, and the like. Embodiments may also be at least partly implemented as instructions contained in or on a non-transitory computer-readable medium, which may be read and executed by one or more processors to enable performance of the operations described herein.

The system memory 806 may include various types of computer-readable storage media in the form of one or more higher speed memory units, such as read-only memory (ROM), random-access memory (RAM), dynamic RAM (DRAM), Double-Data-Rate DRAM (DDRAM), synchronous DRAM (SDRAM), static RAM (SRAM), programmable ROM (PROM), erasable programmable ROM (EPROM), electrically erasable programmable ROM (EEPROM), flash memory, polymer memory such as ferroelectric polymer memory, ovonic memory, phase change or ferroelectric memory, silicon-oxide-nitride-oxide-silicon (SONOS) memory, magnetic or optical cards, an array of devices such as Redundant Array of Independent Disks (RAID) drives, solid state memory devices (e.g., USB memory, solid state drives (SSD) and any other type of storage media suitable for storing information. In the illustrated embodiment shown in FIG. 8, the system memory 806 can include non-volatile memory 810 and/or volatile memory 812. A basic input/output system (BIOS) can be stored in the non-volatile memory 810.

The computer 802 may include various types of computer-readable storage media in the form of one or more lower speed memory units, including an internal (or external) hard disk drive (HDD) 814, a magnetic floppy disk drive (FDD) 816 to read from or write to a removable magnetic disk 818, and an optical disk drive 820 to read from or write to a removable optical disk 822 (e.g., a CD-ROM or DVD). The HDD 814, FDD 816 and optical disk drive 820 can be connected to the system bus 808 by a HDD interface 824, an FDD interface 826 and an optical drive interface 828, respectively. The HDD interface 824 for external drive implementations can include at least one or both of Universal Serial Bus (USB) and IEEE 1394 interface technologies.

The drives and associated computer-readable media provide volatile and/or nonvolatile storage of data, data structures, computer-executable instructions, and so forth. For example, a number of program modules can be stored in the drives and memory units 810, 812, including an operating system 830, one or more application programs 832, other program modules 834, and program data 836. In one embodiment, the one or more application programs 832, other program modules 834, and program data 836 can include, for example, the various applications and/or components of the system 100.

A user can enter commands and information into the computer 802 through one or more wire/wireless input devices, for example, a keyboard 838 and a pointing device, such as a mouse 840. Other input devices may include microphones, infra-red (IR) remote controls, radio-frequency (RF) remote controls, game pads, stylus pens, card readers, dongles, finger print readers, gloves, graphics tablets, joysticks, keyboards, retina readers, touch screens (e.g., capacitive, resistive, etc.), trackballs, trackpads, sensors, styluses, and the like. These and other input devices are often connected to the processing unit 804 through an input device interface 842 that is coupled to the system bus 808, but can be connected by other interfaces such as a parallel port, IEEE 1394 serial port, a game port, a USB port, an IR interface, and so forth.

A monitor 844 or other type of display device is also connected to the system bus 808 via an interface, such as a video adaptor 846. The monitor 844 may be internal or external to the computer 802. In addition to the monitor 844, a computer typically includes other peripheral output devices, such as speakers, printers, and so forth.

The computer 802 may operate in a networked environment using logical connections via wire and/or wireless communications to one or more remote computers, such as a remote computer 848. The remote computer 848 can be a workstation, a server computer, a router, a personal computer, portable computer, microprocessor-based entertainment appliance, a peer device or other common network node, and typically includes many or all of the elements described relative to the computer 802, although, for purposes of brevity, only a memory/storage device 850 is illustrated. The logical connections depicted include wire/wireless connectivity to a local area network (LAN) 852 and/or larger networks, for example, a wide area network (WAN) 854. Such LAN and WAN networking environments are commonplace in offices and companies, and facilitate enterprise-wide computer networks, such as intranets, all of which may connect to a global communications network, for example, the Internet.

When used in a LAN networking environment, the computer 802 is connected to the LAN 852 through a wire and/or wireless communication network interface or adaptor 856. The adaptor 856 can facilitate wire and/or wireless communications to the LAN 852, which may also include a wireless access point disposed thereon for communicating with the wireless functionality of the adaptor 856.

When used in a WAN networking environment, the computer 802 can include a modem 858, or is connected to a communications server on the WAN 854, or has other means for establishing communications over the WAN 854, such as by way of the Internet. The modem 858, which can be internal or external and a wire and/or wireless device, connects to the system bus 808 via the input device interface 842. In a networked environment, program modules depicted relative to the computer 802, or portions thereof, can be stored in the remote memory/storage device 850. It will be appreciated that the network connections shown are exemplary and other means of establishing a communications link between the computers can be used.

The computer 802 is operable to communicate with wire and wireless devices or entities using the IEEE 802 family of standards, such as wireless devices operatively disposed in wireless communication (e.g., IEEE 802.8 over-the-air modulation techniques). This includes at least Wi-Fi (or Wireless Fidelity), WiMax, and Bluetooth™ wireless technologies, among others. Thus, the communication can be a predefined structure as with a conventional network or simply an ad hoc communication between at least two devices. Wi-Fi networks use radio technologies called IEEE 802.8x (a, b, g, n, etc.) to provide secure, reliable, fast wireless connectivity. A Wi-Fi network can be used to connect computers to each other, to the Internet, and to wire networks (which use IEEE 802.3-related media and functions).

Figure 9:
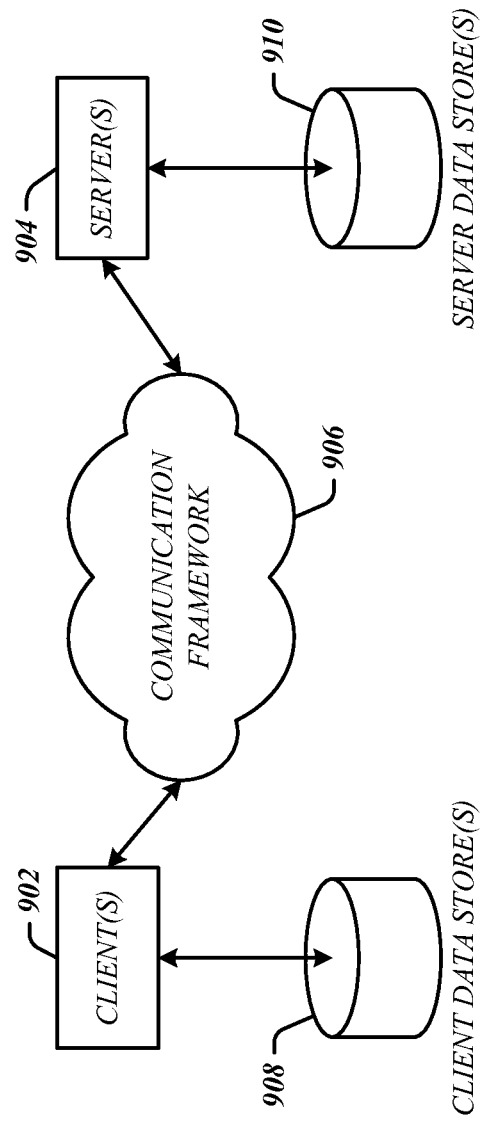
FIG. 9 illustrates an embodiment of a communications architecture.

FIG. 9 illustrates a block diagram of an exemplary communications architecture 900 suitable for implementing various embodiments as previously described. The communications architecture 900 includes various common communications elements, such as a transmitter, receiver, transceiver, radio, network interface, baseband processor, antenna, amplifiers, filters, power supplies, and so forth. The embodiments, however, are not limited to implementation by the communications architecture 900.

As shown in FIG. 9, the communications architecture 900 comprises includes one or more clients 902 and servers 904. The clients 902 may implement the client device 910. The servers 904 may implement the server device 950. The clients 902 and the servers 904 are operatively connected to one or more respective client data stores 908 and server data stores 910 that can be employed to store information local to the respective clients 902 and servers 904, such as cookies and/or associated contextual information.

The clients 902 and the servers 904 may communicate information between each other using a communication framework 906. The communications framework 906 may implement any well-known communications techniques and protocols. The communications framework 906 may be implemented as a packet-switched network (e.g., public networks such as the Internet, private networks such as an enterprise intranet, and so forth), a circuit-switched network (e.g., the public switched telephone network), or a combination of a packet-switched network and a circuit-switched network (with suitable gateways and translators).

The communications framework 906 may implement various network interfaces arranged to accept, communicate, and connect to a communications network. A network interface may be regarded as a specialized form of an input output interface. Network interfaces may employ connection protocols including without limitation direct connect, Ethernet (e.g., thick, thin, twisted pair 10/100/1000 Base T, and the like), token ring, wireless network interfaces, cellular network interfaces, IEEE 802.11a-x network interfaces, IEEE 802.16 network interfaces, IEEE 802.20 network interfaces, and the like. Further, multiple network interfaces may be used to engage with various communications network types. For example, multiple network interfaces may be employed to allow for the communication over broadcast, multicast, and unicast networks. Should processing requirements dictate a greater amount speed and capacity, distributed network controller architectures may similarly be employed to pool, load balance, and otherwise increase the communicative bandwidth required by clients 902 and the servers 904. A communications network may be any one and the combination of wired and/or wireless networks including without limitation a direct interconnection, a secured custom connection, a private network (e.g., an enterprise intranet), a public network (e.g., the Internet), a Personal Area Network (PAN), a Local Area Network (LAN), a Metropolitan Area Network (MAN), an Operating Missions as Nodes on the Internet (OMNI), a Wide Area Network (WAN), a wireless network, a cellular network, and other communications networks.

The embodiments, as previously described, may be implemented using various hardware elements, software elements, or a combination of both. Examples of hardware elements may include devices, logic devices, components, processors, microprocessors, circuits, processor circuits, circuit elements (e.g., transistors, resistors, capacitors, inductors, and so forth), integrated circuits, application specific integrated circuits (ASIC), programmable logic devices (PLD), digital signal processors (DSP), field programmable gate array (FPGA), memory units, logic gates, registers, semiconductor device, chips, microchips, chip sets, and so forth. Examples of software elements may include software components, programs, applications, computer programs, application programs, system programs, software development programs, machine programs, operating system software, middleware, firmware, software modules, routines, subroutines, functions, methods, procedures, software interfaces, application program interfaces (API), instruction sets, computing code, computer code, code segments, computer code segments, words, values, symbols, or any combination thereof. Determining whether an embodiment is implemented using hardware elements and/or software elements may vary in accordance with any number of factors, such as desired computational rate, power levels, heat tolerances, processing cycle budget, input data rates, output data rates, memory resources, data bus speeds and other design or performance constraints, as desired for a given implementation.

In some embodiments, an element is defined as a specific structure performing one or more operations. It may be appreciated, however, that any element defined as a specific structure performing a specific function may be expressed as a means or step for performing the specified function without the recital of structure, material, or acts in support thereof, and such means or step is meant to cover the corresponding structure, material, or acts described in the detailed description and equivalents thereof. The embodiments are not limited in this context.

Some embodiments may be described using the expression "one embodiment" or "an embodiment" along with their derivatives. These terms mean that a particular feature, structure, or characteristic described in connection with the embodiment is included in at least one embodiment. The appearances of the phrase "in one embodiment" in various places in the specification are not necessarily all referring to the same embodiment. Further, some embodiments may be described using the expression "coupled" and "connected" along with their derivatives. These terms are not necessarily intended as synonyms for each other. For example, some embodiments may be described using the terms "connected" and/or "coupled" to indicate that two or more elements are in direct physical or electrical contact with each other. The term "coupled," however, may also mean that two or more elements are not in direct contact with each other, but yet still co-operate or interact with each other.

It is emphasized that the Abstract of the Disclosure is provided to allow a reader to quickly ascertain the nature of the technical disclosure. It is submitted with the understanding that it will not be used to interpret or limit the scope or meaning of the claims. In addition, in the foregoing Detailed Description, it can be seen that various features are grouped together in a single embodiment for the purpose of streamlining the disclosure. This method of disclosure is not to be interpreted as reflecting an intention that the claimed embodiments require more features than are expressly recited in each claim. Rather, as the following claims reflect, inventive subject matter lies in less than all features of a single disclosed embodiment. Thus the following claims are hereby incorporated into the Detailed Description, with each claim standing on its own as a separate embodiment. In the appended claims, the terms "including" and "in which" are used as the plain-English equivalents of the respective terms "comprising" and "wherein," respectively. Moreover, the terms "first," "second," "third," and so forth, are used merely as labels, and are not intended to impose numerical requirements on their objects.

What has been described above includes examples of the disclosed architecture. It is, of course, not possible to describe every conceivable combination of components and/or methodologies, but one of ordinary skill in the art may recognize that many further combinations and permutations are possible. Accordingly, the novel architecture is intended to embrace all such alterations, modifications and variations that fall within the spirit and scope of the appended claims.

What is claimed is:

1. A computer-implemented method, comprising:
   receiving an electronic communication comprising a source document having unknown processing requirements;
   creating a new source document type to process the source document and preserve referential integrity in a database by:
      utilizing a set of extension points in computer memory to create a source document header relation with source document header information and a source document line relation with source document line information for a previous source document type, the source document header information and the source document line information being operative to reference at least a portion of the source document for process logic that is specific for use with the previous source document type, and
      defining the new source document type with a non-overlapping foreign key reference to the source document header relation; and
   storing the source document in the database by using the source document header relation and the source document line relation to reference the source document in that database.

2. The computer-implemented method of claim 1, wherein the source document header information including a source document header record identifier field and a source relation type field.

3. The computer-implemented method of claim 1, wherein the source document line information including a source document line record identifier field, a source document header field, and a source relation type field.

4. The computer-implemented method of claim 1, comprising receiving a request to create a source document of the new source document type.

5. The computer-implemented method of claim 1, comprising storing a document header relation with document header information for a source document of the new source document type, the document header information including a source document header field of type source document header record identifier.

6. The computer-implemented method of claim 1, comprising storing a document line relation with document line information for a source document of the new source document type, the document line information including a source document line field of type source document line record identifier.

7. The computer-implemented method of claim 1, comprising providing a source document framework for referencing source documents of source document types in the database using non-overlapping foreign key constraints.

8. At least one computer-readable storage device comprising instructions that, when executed, cause a system to:
   receive an electronic communication comprising a source document having unknown processing requirements;
   create a new source document type to process the source document and preserve referential integrity in a database by utilizing a set of extension points in computer memory to create a source document header relation with source document header information and a source document line relation with source document line information for a previous source document type, the source document header information and the source document line information being operative to reference at least a portion of the source document for process logic that is specific for use with the previous source document type and defining the new source document type with a non-overlapping foreign key reference to the source document header relation; and
   store the source document in the database by using the source document header relation and the source document line relation to reference the source document in that database.

9. The computer-readable storage device of claim 8, wherein the source document header information including a source document header record identifier field and a source relation type field.

10. The computer-readable storage device of claim 8, wherein the source document line information including a source document line record identifier field, a source document header field, and a source relation type field.

11. The computer-readable storage device of claim 8, comprising instructions that when executed cause the system to receive a request to create a source document of the new source document type.

12. The computer-readable storage device of claim 8, comprising instructions that when executed cause the system to store a document header relation with document header information for a source document of the new source document type, the document header information including a source document header field of type source document header record identifier.

13. The computer-readable storage device of claim 8, comprising instructions that when executed cause the system to store a document line relation with document line information for a source document of the new source document type, the document line information including a source document line field of type source document line record identifier.

14. The computer-readable storage device of claim 8, comprising instructions that when executed cause the system to provide a source document framework for referencing source documents of source document types in the database using non-overlapping foreign key constraints.

15. An apparatus, comprising:
a processor circuit; and
an application arranged for execution by the processor circuit, the application configured to provide services to a database, the application comprising:
  a source document framework component arranged to:
    receive an electronic communication comprising a source having unknown processing requirements,
    create, for an enterprise resource planning (ERP) application, a new source document type from the unknown source document type to process the source document and preserve referential integrity in the database by utilizing a set of extension points in computer memory to create a source document header relation with source document header information and a source document line relation with source document line information for a previous source document type, the source document header information and the source document line information being operative to reference at least a portion of the source document for process logic that is specific for use with the previous source document type and defining the new source document type with a non-overlapping foreign key reference to the source document header relation, and
    store the source document in the database by using the source document header relation and the source document line relation to reference the source document in that database.

16. The apparatus of claim 15, wherein the source document header information including a source document header record identifier field and a source relation type field.

17. The apparatus of claim 15, wherein the source document line information including a source document line record identifier field, a source document header field, and a source relation type field.

18. The apparatus of claim 15, wherein source document framework component further operative to receive a request to create a source document of the new source document type.

19. The apparatus of claim 15, wherein source document framework component further operative to store a document header relation with document header information for a source document of the new source document type, the document header information including a source document header field of type source document header record identifier.

20. The apparatus of claim 15, wherein source document framework component further operative to provide a source document framework for referencing source documents of source document types in the database using non-overlapping foreign key constraints.

* * * * *